United States Patent [19]
Becker et al.

[11] Patent Number: 6,048,684
[45] Date of Patent: Apr. 11, 2000

[54] METHOD FOR THE DETERMINATION OF "SOLUBLE" FIBRIN

[75] Inventors: Udo Becker, Marburg; Konrad Braun, Ebsdorfergrund; Norbert Heimburger, Marburg, all of Germany

[73] Assignee: Dade Behring Marburg GmbH, Marburg, Germany

[21] Appl. No.: 07/727,387

[22] Filed: Jul. 5, 1991

Related U.S. Application Data

[63] Continuation of application No. 07/240,649, Sep. 6, 1988, abandoned.

[30] Foreign Application Priority Data

Sep. 8, 1987 [DE] Germany .............................. 37 30 059

[51] Int. Cl.$^7$ ........................ G01N 33/53; G01N 33/542; G01N 33/543; C12Q 1/56
[52] U.S. Cl. .............................. 435/4; 435/7.9; 435/7.94; 435/13; 435/7.1; 435/7.92; 436/518; 436/821; 530/382; 530/387.1
[58] Field of Search .................................... 435/7.1, 7.92, 435/7.9, 7.94, 13, 4; 436/518, 821; 530/382, 387.1

[56] References Cited

U.S. PATENT DOCUMENTS

| | | | |
|---|---|---|---|
| 4,366,241 | 12/1982 | Tom et al. ........................... | 435/810 X |
| 4,642,285 | 2/1987 | Halbert ......................................... | 435/7 |
| 4,914,040 | 4/1990 | Lenz et al. .............................. | 436/548 |

OTHER PUBLICATIONS

Stemberger et al, "Determination of Soluble Fibrin Monomer Complexes by Adsorption on Immobilized Fibrinogen", in *Thrombos, Haemostas* (Stuttg.) pp. 574–581 (1978).

Chemical Abstract 104:17365; Scheefers–Borchel et al, "Determination of Fibrin with Fibrin–Specific Antibodies", in EP 152612, Published Aug. 28, 1985.

Stemberger, AW et al. 1978. Determination of Soluble Fibrin Monomer Complexes by Adsorption on Immobilized Fibrinogen. Thromb. Haemost. 39 574(abs).

Matsueda, G. et al 1983. Monoclonal Antibodies to a Synthetic Fibrin–Like Peptide Bind to Fibrin but not Fibrinogen. Science 222 1129.

Nakane, P. et al. 1974. Peroxidase–Labeled Antibody. A New Method of Conjugation. J. Histo. Cytochem. 22 1084.

F.A. Breen et al., Ann. Intern. Med., 69:1197–1206 (1968).

S. Niewiarowski and V. Gurewich, J. Lab. Clin. Med., 77:665–676 (1971).

B. Wiman et al., Thromb. Haemostas., 55:189–193 (1986).

U. Scheefers–Borchel et al., Proc. Natl. Acad. Sci. USA, 82:7091–7095 (1985).

N.U. Bang et al., Thromb. and Bleeding Disorders, Thieme Vlg., pp. 222–247 (1971).

S. Avrameas and T. Ternynck, Immunochem., 6:53–66 (1969).

A. Bini et al., Chemical Abstracts, 90:83069 (1979).

P.K. Lund et al., Chemical Abstracts, 90:21837 (1980).

R.A. Schifreen et al., Clin. Chem. 31:468–73 (1985).

*Primary Examiner*—James C. Housel
*Assistant Examiner*—V. Ryan
*Attorney, Agent, or Firm*—Finnegan, Henderson, Farabow, Garrett & Dunner, L.L.P.

[57] ABSTRACT

A method for the determination of soluble fibrin in a body fluid of a species is described, entailing use of a binding partner which is bound to a solid phase, and of a labeled bioaffinity binding partner, for fibrin.

5 Claims, No Drawings

METHOD FOR THE DETERMINATION OF "SOLUBLE" FIBRIN

This application is a continuation of application Ser. No. 07/240,649, filed Sep. 6, 1988 now abandoned.

The invention relates to a method for the determination of "soluble" fibrin in a body fluid of a species, by use of a bioaffinity binding partner, which is bound to a solid phase, for this fibrin and of another, labeled, bioaffinity binding partner for this fibrin, with this other binding partner being selected such that it does not cross-react with the first.

Detection of an activation of the coagulation system is important in clinical diagnosis. Thus, for example, activation of coagulation may occur after an operation and lead to thrombosis. There are as yet no reliable diagnostic criteria for predicting a thrombotic event.

It may be assumed in all cases that latent coagulation is taking place even before this event but is kept under control by counterregulation of the organism (for example by fibrinolytic processes). There is a need in this phase for diagnostic criteria for recognizing this dangerous situation.

A parameter which might be measured is fibrin which is formed from fibrinogen by the action of thrombin. Fibrin is the material which, where there is a thrombosis, causes the occlusion of the vessel. However, in low concentrations, as occur in the phase of the "prethrombotic state" described above, it is soluble and can be used for the diagnosis of a prethrombotic state by suitable detection methods.

The current belief is that fibrin is attached to fibrinogen and is kept in solution by this. If a particular ratio of fibrin to fibrinogen is exceeded there is formation of insoluble fibrin, the material for the thrombotic occlusion of the vessel.

Hence the object of a method for the detection of soluble fibrin is specific detection of fibrin in the presence of a more or less large excess of fibrinogen.

In general, the methods used for this are ones which reduce the solubility of fibrin: examples used are the so-called ethanol-gelation assay of Breen and Tullis (Ann. Intern. Med. 69, 1197–1206, 1968) and the protamine sulfate assay of Niewiarowski and Gurewich (J. Lab. Clin. Med. 77, 665–676, 1971). Newer methods make use of the property of fibrin of enhancing the enzymatic action of plasminogen activators (B. Wimann and M. Ranby, Thromb. Haemostas. 55, 189–193, 1986). Another approach has been to generate antibodies which are able to recognize the small structural differences between fibrinogen and fibrin (U. Scheefers-Borchel et al., Proc. Natl. Acad. Sci. 82, 7091–7095, 1985).

All the methods mentioned have more or less serious disadvantages, some of which derive from insufficient sensitivity and some from inadequate specificity, or else are too elaborate for routine clinical use.

It has been found, surprisingly, that it is possible to make use of the known fibrinogen-binding property of fibrin to provide a new and surprisingly simple method for the determination of soluble fibrin. It combines a functional property of fibrin, namely that of specific binding to fibrinogen, with an immunological method without a special specific antibody against fibrin being necessary for this.

Hence the invention relates to a method for the determination of "soluble" fibrin in a body fluid of a species, which comprises this body fluid being contacted with a bioaffinity binding partner, which is bound to a solid phase, for the fibrin, the body fluid being separated off, the solid phase being contacted with another, labeled, bioaffinity binding partner for the fibrin, with this other binding partner being selected such that it does not cross-react with the first, and comprises the excess of this other binding partner being separated off, and the amount of "soluble" fibrin being determined from the amount of the label bound to the solid phase.

A preferred method is one in which the binding partner on the solid phase is fibrinogen of another species, and the labeled binding partner is an antibody which reacts with fibrin and has been obtained by immunization of a species, preferably this other species, with fibrinogen or fibrin of the species from which the body fluid originates, and has been labeled.

However, another possible procedure is one in which the binding partner on the solid phase is an antibody against fibrin which has been obtained by immunization with fibrinogen or fibrin, and the labeled binding partner is a labeled fibrinogen of a species other than that whose fibrin is to be determined.

The species from which the body fluid originates is preferably man.

It is expedient for the binding partners to be chosen such that one of the binding partners is a fibrinogen from a species other than that from which the body fluid originates, and the other binding partner is an antibody, directed against fibrin, from this other species, in order to diminish the possibility of a cross-reaction.

If a fibrinogen from a species other than that from which the body fluid originates is bound to the solid phase, it is possible for the body fluid to be contacted with the solid phase in the presence of additional fibrinogen from this other species.

An enzyme is particularly suitable for the labeling.

The invention furthermore relates to the use of fibrinogen from one species for the determination of "soluble" fibrin in a body fluid from another species. A preferred embodiment makes use of fibrinogen which is bound to a solid carrier. It is possible to employ as solid carrier a plastic surface, as used for solid-phase immuno-assays (ELISA), for example microtitration plates, polystyrene tubes or plastic beads. The fibrinogen coating can be applied both by adsorption and covalently. Especially suitable are polystyrene surfaces which can be coated by impregnation with a fibrinogen solution. The fibrinogen solution to be used for the coating is generally employed in a concentration of more than 1 mg/l, the exact concentration not being crucial because the adsorption depends more on the binding capacity of the surface than on the concentration of the solution. The fibrinogen to be used for the coating should not cross-react with the antibody against fibrin used in the assay. This is achieved most simply by using fibrinogen from the same species as employed for preparing the labeled antibodies against the fibrin which is to be determined. Surfaces coated with fibrinogen in this way are then able to adsorb "soluble" fibrin from a body fluid which is introduced. The fluid is separated off, and the surface is washed. It is then possible to detect with an antibody the fibrin adsorbed from the sample. The properties of this antibody should be chosen such that it reacts with the fibrin in the sample but not with the fibrinogen used for coating the plastic surface. If the intention is to determine soluble fibrin in human blood plasma, a suitable antibody is one directed against human fibrinogen or against its degradation products. It is immaterial whether the antibody is polyclonal or monoclonal. The only important point is that it does not cross-react with the fibrinogen used for coating the solid phase. The simplest way to meet this condition is to use antibodies and coating fibrinogen from the same species, because antibodies are not formed against endogenous proteins. The antibodies can be labeled, especially with a radioisotope or, preferably, an enzyme, in order to detect the binding in a known manner. It is likewise possible in a subsequent reaction to use a labeled antibody against the first antibody ("sandwich assay").

It is possible in a special embodiment for fibrinogen to be added to the incubation medium. This compensates for different fibrinogen contents in the samples for investigation. Since soluble fibrin is kept in solution by fibrinogen, it is conceivable that different contents of fibrinogen in the sample might have an effect on the result of measurement. This effect can therefore be eliminated by addition of fibrinogen. It is not appropriate to use human fibrinogen for this purpose when soluble human fibrin is to be determined, because purified human fibrinogen may contain traces of soluble fibrin, which would mean interference with the detection method. Hence, it is expedient to use fibrinogen from the species employed to obtain the antibody used, for example rabbit fibrinogen, in order not to obtain a cross-reaction with anti-fibrinogen where the fibrinogen is contaminated with soluble fibrin.

The invention is explained by the examples which follow.

EXAMPLE 1

Coating of polystyrene tubes with rabbit fibrinogen Rabbit fibrinogen (prepared by the method of R. M. Huseby and N. Bang: Fibrinogen, in Thrombosis and Bleeding Disorders, Thieme-Verlag Stuttgart, N. Bang, F. Beller, E. Deutsch and E. Mammen (Eds.) pages 222–247, 1971), 20 mg/l was dissolved in 0.01 mol/l phosphate buffer, pH 7.4, and 0.25 ml samples were placed in polystyrene tubes (supplied by Greiner). Incubation overnight was followed by several washes with 0.05 mol/l Tris/citric acid buffer, pH 7.4, and the tubes were dried in a drying cabinet over silica gel at room temperature. After the drying, they were sealed air- and moisture-tight in aluminum envelopes until subsequently used.

EXAMPLE 2

Preparation of a conjugate of rabbit anti-human fibrinogen and peroxidase

Rabbit antiserum against human fibrinogen (Behringwerke, Product No. ORCH) was mixed with the same volume of saturated ammonium sulfate solution, and the precipitate was spun down. The precipitate was washed twice with 50% strength ammonium sulfate solution and then dissolved in a little 0.2 mol/l Na phosphate, pH 8.2, and dialyzed against the same buffer. This antibody solution was then coupled with peroxidase (Boehringer Mannheim, Order No. 108090) in a known manner. For the procedure, see S. Avrameas, Immunochemistry 6, 43 (1969). The conjugate prepared in this way was prediluted to a dilution suitable for the assay and stored in portions at −70° C.

EXAMPLE 3

Production of blood plasma containing soluble fibrin

Citrated human plasma, for example standard human plasma (Behringwerke, Order No. ORKL), was mixed with 0.05 IU/ml thrombin, for example assay thrombin (Behringwerke, Order No. ORHT), and 0.2 ml aliquots were pipetted after specified times into 0.02 ml of a mixture of hirudin 10 U/ml and heparin 20 U/ml to stop the thrombin reaction. The comparison used was a plasma sample which had been mixed with physiological saline in place of thrombin.

EXAMPLE 4

Procedure for an assay for soluble fibrin.

The samples prepared as in Example 3 were diluted 1:100 with a Tris buffer (0.05 ml/l, pH 7.4, containing TWEEN® 80 0.5%, EDTA 5 mmol/l and ANTAGOSAN® (Behringwerke AG aprotinin solution) 70 KIU/ml) before the assay. 0.2 ml of the prediluted samples was pipetted into each of the tubes coated with rabbit fibrinogen, prepared as in Example 1, and incubated at room temperature for 2 hours. The liquid was then removed by aspiration, and the tubes were washed three times with buffer (for example Enzygnost washing buffer from Behringwerke, Order No. OSNK). 0.2 ml of the antibody conjugate prepared as in Example 2 was then pipetted into each tube and incubated at room temperature for 2 hours. Three washes were again carried out, and 0.2 ml of substrate solution (for example o-phenylenediamine substrate solution, Behringwerke, Order No. OSNK) was introduced into each tube. After 10 min at room temperature, the reaction was stopped with 1 ml of 2 normal sulfuric acid in each tube, and the absorbance of these samples at 492 nm was measured in a photometer. The absorbance listed in the table below were obtained, which show that soluble fibrin was produced in the plasma by the action of thrombin, and that the amount of soluble fibrin depends on the duration of exposure to thrombin.

TABLE 1

| Reaction times in seconds | Thrombin kinetics (Ext. 492 nm) | Phys. NaCl control (Ext. 492 nm) |
| --- | --- | --- |
| 0 | 0.335 | 0.301 |
| 10 | 0.582 | 0.245 |
| 20 | 0.861 | 0.246 |
| 40 | 1.311 | 0.262 |
| 60 | 1.868 | 0.275 |

EXAMPLE 5

Production of blood plasma with a defined content of soluble fibrin, and determination of the fibrin content 5 ml of human EDTA plasma (2 mg/ml EDTA, trisodium salt) were diluted with 20 ml of physiological saline and warmed to 37° C. Then 0.167 ml of a thrombin solution (30 IU/ml) was added, and the mixture was incubated at 37° C. for 30 min.

The clot was squeezed dry on cellulose and washed three times with physiological saline. It was then dissolved in 2.5 ml of 3 M urea solution, and the solution was centrifuged at 3000×g for 10 min to clarify. Measurement of the absorbance at 280 nm showed a concentration of 3.1 g/l based on a specific absorbance for fibrin of 15.6.

Any thrombin still present was inactivated by addition of hirudin (25 µl of 1000 IU/ml).

1 ml of citrated human plasma containing 2 IU/ml heparin was adjusted to a content of 0.1 mg/ml soluble fibrin using the solution of fibrin in urea prepared above, and further dilutions in geometric series in heparin-containing citrated plasma were prepared therefrom. The concentrations are shown in Table 2.

Then samples were diluted 1:100 in buffer and assayed as described in Example 4.

Table 2 lists the absorbances obtained, which increase as a function of the amount of soluble fibrin. Also entered in Table 2 as controls are the citrated plasma sample mixed with pure urea solution, and a sample in which buffer was used in place of plasma.

TABLE 2

| Sample No. | Content of soluble fibrin in plasma (mg/L) | $A_{405}$ nm |
|---|---|---|
| 1 | 0 | 0.108 |
| 2 | 0.2 | 0.129 |
| 3 | 0.4 | 0.086 |
| 4 | 0.8 | 0.123 |
| 5 | 1.6 | 0.123 |
| 6 | 3.2 | 0.201 |
| 7 | 6.3 | 0.276 |
| 8 | 12.5 | 0.352 |
| 9 | 25.0 | 0.510 |
| 10 | 50.0 | 0.832 |
| 11 | 100.0 | 1.205 |
| Controls | | |
| Plasma/urea | — | 0.102 |
| Buffer | — | 0.002 |

We claim:

1. A method for the determination of soluble fibrin in a body fluid, comprising the steps of:

a) binding fibrinogen to a solid phase support;

b) incubating a sample of said body fluid with the solid phase bound fibrinogen whereby the soluble fibrin specifically binds to the solid phase bound fibrinogen, immobilizing the soluble fibrin;

c) separating said immobilized soluble fibrin from said body fluid;

d) providing an antibody able to react immunochemically with the immobilized soluble fibrin, said antibody being covalently linked to a detectable label to form a labeled antibody capable of immunochemically reacting with the immobilized soluble fibrin;

e) contacting the labeled antibody with the solid phase bound fibrinogen which has been pre-incubated with said body fluid to specifically bind the label to said immobilized soluble fibrin;

f) detecting said bound label; and g) determining the concentration of soluble fibrin in the body fluid from said bound label wherein said antibody covalently linked to said detectable label is derived from an animal of the same species from which the fibrinogen is obtained but which is not the same species as the animal from which the body fluid is taken.

2. A method for the determination of soluble fibrin in a body fluid, comprising the steps of:

a) binding an antibody able to react immunochemically with soluble fibrin to a solid phase support;

b) incubating a sample of said body fluid with the solid phase bound antibody whereby the soluble fibrin specifically binds to the solid phase bound antibody, immobilizing the soluble fibrin;

c) separating said immobilized soluble fibrin from said body fluid;

d) providing fibrinogen, said fibrinogen being covalently linked to a detectable label to form a labeled fibrinogen capable of specifically reacting with the immobilized soluble fibrin;

e) contacting the labeled fibrinogen with the solid phase bound antibody which has been pre-incubated with said body fluid to specifically bind the label to said immobilized soluble fibrin;

f) detecting said bound label; and g) determining the concentration of soluble fibrin in the body fluid from said bound label wherein said fibrinogen covalently linked to said detectable label is derived from an animal of the same species from which the antibody is obtained but which is not the same species as the animal from which the body fluid is taken.

3. The method according to claim 1 wherein the antibody has been obtained through immunization with fibrin or fibrinogen derived from an animal of the same species from which the body fluid is taken.

4. The method according to claim 1 wherein the body fluid is taken from a human.

5. The method according to claim 1 wherein the antibody is labeled with an enzyme.

* * * * *